(12) United States Patent
Farnaby et al.

(10) Patent No.: US 9,750,748 B2
(45) Date of Patent: Sep. 5, 2017

(54) PYRIDAZINONES AS DAAO ENZYME INHIBITORS

(71) Applicant: TAKEDA PHARMACEUTICAL COMPANY LIMITED, Osaka (JP)

(72) Inventors: William Farnaby, Cambridge (GB); Charlotte Fieldhouse, Cambridge (GB); Katherine Hazel, Cambridge (GB); Catrina Kerr, Dundee (GB); Natasha Kinsella, Kampala (UG); David Livermore, Cambridge (GB); Kevin Merchant, Cambridge (GB); David Miller, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/652,484

(22) PCT Filed: Dec. 17, 2013

(86) PCT No.: PCT/GB2013/000552
§ 371 (c)(1),
(2) Date: Jun. 16, 2015

(87) PCT Pub. No.: WO2014/096757
PCT Pub. Date: Jun. 24, 2014

(65) Prior Publication Data
US 2015/0329495 A1 Nov. 19, 2015

(30) Foreign Application Priority Data

Dec. 17, 2012 (GB) .................................. 1222711.2

(51) Int. Cl.
| | | |
|---|---|---|
| *A61K 31/55* | (2006.01) | |
| *C07D 405/04* | (2006.01) | |
| *A61K 31/501* | (2006.01) | |
| *C07D 403/04* | (2006.01) | |
| *C07D 237/20* | (2006.01) | |
| *C07D 401/04* | (2006.01) | |
| *A61K 45/06* | (2006.01) | |
| *A61K 31/50* | (2006.01) | |
| *C07D 237/16* | (2006.01) | |
| *C07D 237/22* | (2006.01) | |
| *A61K 31/277* | (2006.01) | |
| *A61K 31/496* | (2006.01) | |
| *A61K 31/519* | (2006.01) | |
| *A61K 31/53* | (2006.01) | |
| *A61K 31/551* | (2006.01) | |
| *A61K 31/554* | (2006.01) | |
| *A61K 33/00* | (2006.01) | |

(52) U.S. Cl.
CPC ............ *A61K 31/55* (2013.01); *A61K 31/277* (2013.01); *A61K 31/496* (2013.01); *A61K 31/50* (2013.01); *A61K 31/501* (2013.01); *A61K 31/519* (2013.01); *A61K 31/53* (2013.01); *A61K 31/551* (2013.01); *A61K 31/554* (2013.01); *A61K 33/00* (2013.01); *A61K 45/06* (2013.01); *C07D 237/16* (2013.01); *C07D 237/20* (2013.01); *C07D 237/22* (2013.01); *C07D 401/04* (2013.01); *C07D 403/04* (2013.01); *C07D 405/04* (2013.01)

(58) Field of Classification Search
CPC .................................................... C07D 400/13
See application file for complete search history.

(56) References Cited

U.S. PATENT DOCUMENTS

| | | |
|---|---|---|
| 4,193,916 A | 3/1980 | Back et al. |
| 4,743,685 A | 5/1988 | Breuer et al. |
| 5,244,890 A | 9/1993 | Yamanaka et al. |
| 5,401,734 A | 3/1995 | Yamanaka et al. |
| 5,532,354 A | 7/1996 | Yamanaka et al. |
| 5,962,480 A | 10/1999 | Moriguchi et al. |
| 2010/0022526 A1 | 1/2010 | Lamberth et al. |

(Continued)

FOREIGN PATENT DOCUMENTS

| | | |
|---|---|---|
| BE | 859 477 | 4/1978 |
| DE | 2 745 024 | 4/1978 |

(Continued)

OTHER PUBLICATIONS

Yakugaku et al., Syntheses of N-heterocyclic compounds. VIII. Hydrolysis of 2-phenylpyrimido[4,5-d]pyridazine derivatives Yakugaku Zasshi (1972), 92(11), 1312-15 CODEN: YKKZAJ; ISSN: 0031-6903; Japanese.*

(Continued)

*Primary Examiner* — Paul V Ward
(74) *Attorney, Agent, or Firm* — Finnegan, Henderson, Farabow, Garrett & Dunner LLP

(57) ABSTRACT

The present invention provides compounds of formula (I) and pharmaceutically acceptable salts thereof,

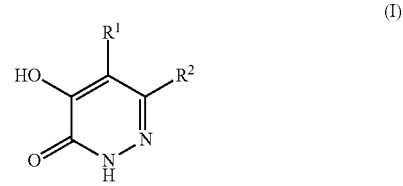

wherein $R^1$ and $R^2$ are as defined in the specification, processes for their preparation, pharmaceutical compositions containing them and their use in therapy.

18 Claims, No Drawings

(56) References Cited

U.S. PATENT DOCUMENTS

| | | |
|---|---|---|
| 2013/0052281 A1 | 2/2013 | Farnaby et al. |
| 2014/0243353 A1 | 8/2014 | Farnaby et al. |
| 2014/0248378 A1 | 9/2014 | Cockcroft et al. |
| 2015/0030704 A1 | 1/2015 | Farnaby et al. |

FOREIGN PATENT DOCUMENTS

| | | |
|---|---|---|
| EP | 0 180 298 | 5/1986 |
| EP | 0 593 110 | 4/1994 |
| EP | 2 314 586 | 4/2011 |
| GB | 2 025 416 | 1/1980 |
| JP | 61-57563 | 3/1986 |
| JP | 62-84082 | 4/1987 |
| JP | 64-29367 | 1/1989 |
| JP | 1-202875 | 8/1989 |
| JP | 1-261392 | 10/1989 |
| JP | 2002-028187 | 1/1990 |
| JP | 5-255344 | 10/1993 |
| JP | 2009-025234 | 1/1997 |
| JP | 2001-519416 | 10/2001 |
| JP | 2007-517056 | 6/2007 |
| JP | 2009-542683 | 12/2009 |
| WO | WO 95/11235 | 4/1995 |
| WO | WO 02/053543 | 7/2002 |
| WO | WO 03/047558 A2 | 6/2003 |
| WO | WO 03/062233 | 7/2003 |
| WO | WO 2004/094408 | 11/2004 |
| WO | WO 2005/061458 | 7/2005 |
| WO | WO 2005/066135 | 7/2005 |
| WO | WO 2006/135828 | 12/2006 |
| WO | WO 2008/069453 | 7/2008 |
| WO | WO 2008/115381 A1 | 9/2008 |
| WO | WO 2008/116301 | 10/2008 |
| WO | WO 2008/156607 | 12/2008 |
| WO | WO 2009/020814 | 2/2009 |
| WO | WO 2010/017418 | 2/2010 |
| WO | WO 2010/058314 A1 | 5/2010 |
| WO | WO 2011/046920 | 4/2011 |
| WO | WO 2011/109254 | 9/2011 |
| WO | WO 2011/109261 | 9/2011 |
| WO | WO 2011/109267 | 9/2011 |
| WO | WO 2013/003383 A1 | 1/2013 |
| WO | WO 2013/004995 | 1/2013 |
| WO | WO 2013/004996 | 1/2013 |
| WO | WO 2013/027000 A1 | 2/2013 |
| WO | WO 2013/073577 A1 | 5/2013 |
| WO | WO 2015/132608 | 9/2015 |

OTHER PUBLICATIONS

Bluth et al., Pharmacological characterization of novel pyridazines. Part 2: Analgetic, antipyretic and antiphlogistic activity Pharmazie (1981), 36(11), 775-7 CODEN: PHARAT; ISSN: 0031-7144; German.*
U.S. Appl. No. 13/591,659, filed on Aug. 22, 2012.
U.S. Appl. No. 14/131,337, filed on Jan. 7, 2014.
U.S. Appl. No. 14/131,343, filed on Jan. 7, 2014.
U.S. Appl. No. 14/240,045, filed on Feb. 21, 2014.
U.S. Appl. No. 14/358,162, filed on May 14, 2014.
Adage T., et 31,, "In vitro and in vivo pharmacological profile of AS057278, a selective D-amino acid oxidase inhibitor with potential anti-psychotic," J. Eur. Neuropsychopharmacology (2008) 18, 200-214.
Division of Medicinal Chemistry Scientific Abstracts for the 244th National Meeting and Exposition, Aug. 19-23, 2012, Philadelphia, PA; publication date Jul. 6, 2012 (see Entry MEDI 98).
Duplantier A., et al., "Discovery, SAR, and Pharmacokinetics of a Novel-3-Hydroxyquinolin-2(1H)-one Series of Potent D-Amino Acid Oxidase (DAAO) Inhibit" J. Med. Chem., 2009, 52, 3576-3585.
Dvumaev, K. M. at at, "Aminomethyiation of 2,3-dihydroxy- and 3-hydroxy-2-methoxypyridine," Tr, Samarkand. Univ., 1970, No. 180, pp. 180-14 (CAS Database Accession No. 1972:564402).

English Abstract of Aroyan, A. A. et al. Pyrimidine derivatives. XXXVI. Synthesis and IR and mass spectra of 2-(p-alkoxybenzyl)-4,5-dihydroxypyrimidines, Arnyanskl Khimicheskii Ehurnal, vol. 27, No. 11, 974, 963-968; CAS Database Accession No. 1975:140063 CAPLUS.
English Abstract of BE 859477.
Ferraris D., et al., "Synthesis and Biological Evaluation of D-Amino Acid Oxidase Inhibitors," J. Med Chem., 2008, 51, pp. 3357-3359.
Hackarn, D. G. et al., "Translation of Research Evidence From Animals to Humans," J American Medical Association, 296(14), 2006, pp. 1731-1732.
Hondo, et al., "4-Hydroxypyridazin-3(2H)-one derivatives as novel D-Amino acid oxidase inhibitors", J. Med. Chem. May 9, 2013; 56(9); 3582-92 (web publication date Apr. 8, 2013).
International Search Report and Written Opinion, PCT/GB2012/000672, mailed Oct. 1, 2012.
International Search Report, PCT/GB2012/000573, mailed Sep. 10, 2012.
International Search Report, PCT/GB2012/000574, mailed Oct. 11, 2012.
Jordan, V.C., "Tamoxifen: A most unlikely pioneering medicine," Nature Reviews: Drug Discovery, 2, 2003, 205-213.
Nakamura et al., "Studies on Prototropic Tautomerism in Nitrogen Heterocyclic Compounds, I. The Mannich Reaction of 2(1H)-Pyridone and 3-Hydroxy-2(11-1)-pyridone)," Chem. Pharm. Bull., vol. 16, No. 8, 1968, 1446-1471 (1968).
Nakamura et al, "Studies on Prototropic Tautomerism in Nitrogen Heterocyclic Compounds, II, A Ring-Chain Tautomerism in 3-Hydroxy-6-(2-oxocycloalky)-methyl-2(1H)-pyridone and 3-Hydroxy-6-(3-oxoalkyl)-2(1H)-pyridone Derivatives," Chem. Pharm. Bull., vol. 1 7 , No. 3, 1969, 425-433 (1969).
Office Action (Restriction Requirement) dated Jan. 24, 2013, in U.S. Appl. No. 13/591,859.
Office Action dated Sep. 19, 2013, in U.S. Appl. No. 13/591,859.
Office Action dated Mar. 19, 2015, in U.S. Appl. No. 14/131,343.
Office Action (Restriction Requirement) dated Mar. 16, 2015, in U.S. Appl. No. 14/240,045.
Office Action dated Mar. 18, 2015, in U.S. Appl. No. 14/358,162.
Office Action dated May 8, 2015 in U.S. Appl. No. 13/591,859.
Office Action dated Jun. 12, 2015, in U.S. Appl. No. 14/240,045.
Notice of Allowance dated Jul. 9, 2015, in U.S. Appl. No. 14/131,343.
Notice of Allowance dated Jul. 17, 2015, in U.S. Appl. No. 14/358,162.
Sunagawa et al., "Synthesis and Antibacterial Activity of Novel Carbapertems with a Catechol or Hydroxypyridone moiety", Journal of Antibiotics (1994) 47(11) 1354-58.
Sparey T. et al., "The discovery of fused pyrrole carboxylic acids as novel, potent D-amino acid oxidase (DAO) inhibitors," Bioorganic & Medicinal Chemistry Letters, 2008 18, pp. 3386-3391.
R. Bluth, "Pharmacological Characterization of Novel Pyridazines," Pharmazie, vol. 36 No. 11, pp. 775-777 (1981).
Yucheng Feng et al., "Photolytic and Microbial Degradation of 3,5,6-trichloro-2-pyridinol," Environmental Toxicology and Chemistry, vol. 17, No. 5, pp. 814-819 (1998).
International Search Report for International Patent Application No. PCT/JP2012/079521, dated Jan. 22, 2013.
English language abstract of JP 02-028187, filed Jun. 6, 1989.
English language abstract of JP 09-025234, filed Jul. 12, 1995.
English language abstract of JP 62-84082.
English language abstract of JP 2007-517056.
Corrected Notice of Allowance dated Aug. 19, 2015, in U.S. Appl. No. 14/358,162.
International Search Report for PCT/GB2013/000552, Mar. 20, 2014.
Bluth, R., "Pharmakologische Charakterisierung neuartiger Pyridazine", Die Pharmazi, 1981, 36(11), pp. 775-777. German.
Hieda, Masaru et al, "Studies on the Syntheses of N-Heterocyclic Compounds" VIII. Hydrolysis of 2- Phenylpyrimido[4,5-d]pyridazine Derivatives. Yakugaku Zasshi, 1972, 92(11), pp. 1312-1315. Japanese.

(56) References Cited

OTHER PUBLICATIONS

Smith, Sean M. et al, "The Therapeutic Potential of D-Amino Acid Oxidase (DAAO) Inhibitors", *The Open Medicinal Chemistry Journal*, 2010, 4, pp. 3-9, U.S.
Almond, S.L. et al., "Behavioral and biochemical characterization of a mutant mouse strain lacking D-amino acid oxidase activity and its implications for schizophrenia," MCN Molecular and Cellular Neuroscience, vol. 32, pp. 324-334 (2006).
Hashimoto, Atsushi et al., "Mice lacking D-amino acid oxidase activity display marked attenuation of sterotypy and ataxia induced by MK-801," Brain Research, vol. 1033, pp. 210-215 (2005).
Vree, T.B. et al., "Novel oxidative pathways of sulphapyridine and sulphadiazine by the turtle *Pseudemys scripta elegans*," The Veterinary Quarterly, vol. 13, No. 4, pp. 218-224 (1991).
U.S. Appl. No. 15/123,796, filed Sep. 6, 2016.
Database CA, chemical abstracts service, Database Accession No. 1978:512324.
Japanese Office Action for Japanese Patent Application No. 517912/2014, dated Feb. 24, 2016.
Japanese Office Action for Japanese Patent Application No. 517913/2014, dated Feb. 26, 2016.
Japanese Office Action for Japanese Patent Application No. 526537/2014, dated Feb. 24, 2016.
Machine translation of JP 61-57563.
English language abstract of JP 64-29367.
English language abstract of JP 1-202875.
English language abstract of JP 1-261392.
English language abstract of JP 5-255344.
English language abstract of JP 2001-519416.
English language abstract of JP 2009-542683.
International Search Report and Written Opinion, PCT/GB2015/050654.

\* cited by examiner

PYRIDAZINONES AS DAAO ENZYME INHIBITORS

This application is a national stage filing under 35 U.S.C. §371 of international Application No. PCT/G320131000552 filed on Dec. 17, 2013, which claims priority of Great Britain Patent Application No. 1222711,2, filed Dec. 17, 2012. The contents of these applications are incorporated herein by reference.

The present invention relates to pyridazinone derivatives, processes for their preparation, pharmaceutical compositions containing them and their use in therapy, particularly in the treatment or prevention of conditions having an association with the D-amino acid oxidase enzyme (DAAO).

The hyper-dopaminergic theory has driven schizophrenia drug discovery for decades and has produced notable drugs such as clozapine and olanzapine. Although these medicaments can be highly efficacious against the positive symptoms of schizophrenia and have significantly benefited many patients they are not the complete answer, with fewer or no effects against the negative and cognitive aspects of the disease and with undesired side effect profiles in some cases. Amongst alternative hypotheses the hyper-glutamatergic theory has much merit with the first real evidence coming from the use of PCP (phencyclidine), MK801 or ketamine, direct N-methyl-D-aspartate (NMDA)-receptor antagonists that are able to produce schizophrenia-like symptomatology in healthy human volunteers or exacerbate the clinical signs in schizophrenia patients. However, direct modulation of the NMDA receptor using agonists has not proved successful with excitotoxicity (excessive stimulation by the neurotransmitter) leading to undesirable side effects. An alternative approach is to target the co-agonists required for NMDA receptor activation. These are glycine and serine (D-SER). Attempts to enhance NMDA receptor activity through the use of glycine transporter inhibitors have produced clinical compounds (but no marketed drugs to-date). D-SER is a co-agonist with even greater potency than glycine and so modulation of D-SER may represent an alternative strategy. One way to increase levels of D-SER is to reduce the activity of DAAO, the enzyme which removes it from the synaptic cleft.

DAAO enzyme inhibitors are known in the art. For example, Adage et al., *European Neuropsychopharmacology* 2008, 18, 200-214 have described AS-057278, a small molecule DAAO enzyme inhibitor. Likewise, Sparey et al., *Bioorganic & Medicinal Chemistry Letters*, 2008, 18, 3386-3391 have demonstrated that molecules containing small heterocyclic rings furnished with a carboxylic acid group can inhibit the DAAO enzyme. DAAO inhibitors which avoid the carboxylic acid group have been described by Ferraris et al., *J. Med Chem.* 2008, 51, 3357-3359 and by Duplantier et al., *J. Med Chem.* 2009, 52, 3576-3585. A further series of carboxylic acid-containing DAAO enzyme inhibitors from Sepracore are described in WO 2008/089453.

Yakugaku Zasshi, vol. 92(11), 1972 (Hieda et al) discloses the compound 2,3-dihydro-4-hydroxy-6-morpholinopyridazin-3-one.

Environmental Science & Technology, vol. 46(7), 2012 (Dirany et al) discloses the compound 6-amino-4-hydroxypyridazinone.

We have now discovered a new class of compounds that are DAAO enzyme inhibitors which have desirable activity profiles. The compounds of this invention have beneficial potency, selectivity and/or pharmacokinetic properties.

In accordance with the present invention, there is therefore provided a compound of formula (I)

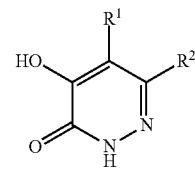

(I)

wherein
$R^1$ represents a hydrogen or fluorine atom or a trifluoromethyl group;
$R^2$ represents a $C_2$-$C_8$ alkyl, $C_3$-$C_8$ cycloalkyl or tetrahydropyranyl group, each of which may be optionally substituted by one or more substituents, or $R^2$ represents a group —$NR^3R^4$;
$R^3$ and $R^4$ each independently represent a hydrogen atom or a $C_1$-$C_6$ alkyl group, or $R^3$ and $R^4$ together with the nitrogen atom to which they are attached form a saturated or unsaturated 4- to 8-membered heterocyclic ring, wherein each alkyl group or the heterocyclic ring may be optionally substituted by one or more substituents; and
wherein the one or more optional substituents in $R^2$, $R^3$ and $R^4$ are independently selected from halogen, hydroxyl, cyano, carboxyl, $C_1$-$C_6$ alkyl, difluoromethyl, trifluoromethyl, $C_1$-$C_6$ alkoxy, difluoromethoxy and trifluoromethoxy; but not including the following compounds:
2,3-dihydro-4-hydroxy-6-morpholinopyridazin-3-one, and
6-amino-4-hydroxy-pyridazinone;
or a pharmaceutically acceptable salt thereof.

In the context of the present specification, unless otherwise stated, an "alkyl" substituent group or an alkyl moiety in a substituent group may be linear or branched. Examples of $C_1$-$C_8$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl, n-hexyl, n-heptyl and n-octyl.

A "cycloalkyl" substituent group/moiety is a saturated hydrocarbyl ring containing, for example, from 3 to 8 carbon atoms, examples of which include cyclopropyl, cyclobutyl, cyclopentyl and cyclohexyl.

It will be understood that if $R^3$ and $R^4$ together with the nitrogen atom to which they are attached form a saturated or unsaturated 4- to 8-membered heterocyclic ring, the ring can be partially or fully unsaturated and thus the ring can have alicyclic or aromatic properties. Furthermore, the heterocyclic ring may contain one or more (e.g. one or two) further ring heteroatoms (e.g. nitrogen, oxygen or sulphur atoms) in addition to the nitrogen atom to which $R^3$ and $R^4$ are attached. Nevertheless, it should be understood that the invention does not encompass any unstable ring structures or any O—O, O—S or S—S bonds. If a substituent is present, it may be attached to any suitable ring atom. Examples of such heterocyclic rings include azetidinyl, pyrrolyl, piperidinyl, morpholinyl, thiomorpholinyl, thiazolyl, piperazinyl, pyrazolyl, pyrazinyl, imidazolyl, isoxazolyl, triazolyl, tetrazolyl and pyridinyl moieties.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In an embodiment of the invention, $R^1$ represents a hydrogen atom.

In an embodiment of the invention, $R^2$ represents a $C_2$-$C_8$, or $C_2$-$C_6$, or $C_2$-$C_4$ alkyl, $C_3$-$C_8$, or $C_3$-$C_7$, or $C_3$-$C_6$ cycloalkyl or tetrahydropyranyl group, each of which may be optionally substituted by one or more (e.g. one, two, three, four or five) substituents independently selected from halogen (e.g. fluorine, chlorine or bromine), hydroxyl, cyano, carboxyl, $C_1$-$C_6$, or $C_1$-$C_4$, or $C_1$-$C_2$ alkyl, difluoromethyl, trifluoromethyl, $C_1$-$C_6$, or $C_1$-$C_4$, or $C_1$-$C_2$ alkoxy, difluoromethoxy and trifluoromethoxy.

Where $R^2$ represents an optionally substituted alkyl group containing 3 or more carbon atoms, the alkyl group is preferably branched, e.g. isopropyl, t-butyl, 2-methylpropyl or 3-methylbutyl.

In another embodiment of the invention, $R^2$ represents a $C_2$-$C_6$ or $C_2$-$C_5$ alkyl group which may be linear or branched.

In still another embodiment, $R^2$ represents a $C_3$-$C_6$ cycloalkyl group.

In yet another embodiment, $R^2$ represents a tetrahydropyranyl group.

Alternatively, $R^2$ may represent a group —$NR^3R^4$ in which $R^3$ and $R^4$ each independently represent a hydrogen atom or a $C_1$-$C_6$, or $C_1$-$C_4$, or $C_1$-$C_2$ alkyl group, or $R^3$ and $R^4$ together with the nitrogen atom to which they are attached form a saturated or unsaturated 4- to 8-, preferably 4- to 6-, membered heterocyclic ring, wherein each alkyl group or the heterocyclic ring may be optionally substituted by one or more substituents (e.g. one, two, three, four or five) substituents independently selected from halogen (e.g. fluorine, chlorine or bromine), hydroxyl, cyano, carboxyl, $C_1$-$C_6$, or $C_1$-$C_4$, or $C_1$-$C_2$ alkyl, difluoromethyl, trifluoromethyl, $C_1$-$C_6$, or $C_1$-$C_4$, or $C_1$-$C_2$ alkoxy, difluoromethoxy and trifluoromethoxy.

In an embodiment of the invention, $R^2$ represents a group —$NR^3R^4$ in which $R^3$ and $R^4$ each independently represent a hydrogen atom or, preferably, a $C_1$-$C_4$ or $C_1$-$C_3$ alkyl group. The alkyl group is advantageously linear.

In a further embodiment, $R^2$ represents a group —$NR^3R^4$ in which $R^3$ and $R^4$ together with the nitrogen atom to which they are attached form an unsaturated or, preferably, saturated 4- to 8-, preferably 4- to 6-, membered heterocyclic ring. In one aspect, the heterocyclic ring contains no further ring heteroatoms in addition to the nitrogen atom to which $R^3$ and $R^4$ are attached (e.g. azetidine, pyrrole or piperidine).

In a preferred embodiment of the invention,
$R^1$ represents a hydrogen atom; and
$R^2$ represents a $C_2$-$C_5$ alkyl, $C_3$-$C_6$ cycloalkyl or tetrahydropyranyl group, or
$R^2$ represents a group —$NR^3R^4$ in which $R^3$ and $R^4$ each independently represent a $C_1$-$C_3$ alkyl group, or $R^3$ and $R^4$ together with the nitrogen atom to which they are attached form a saturated 4- to 6-membered heterocyclic ring.

Examples of compounds of the invention include:
6-Ethyl-4-hydroxypyridazin-3(2H)-one,
4-Hydroxy-6-(3-methylbutyl)pyridazin-3(2H)-one,
6-Cyclopropyl-4-hydroxypyridazin-3(2H)-one,
4-Hydroxy-6-(tetrahydro-2H-pyran-4-yl)pyridazin-3(2H)-one,
4-Hydroxy-6-(2-methylpropyl)pyridazin-3(2H)-one,
6-Cyclopentyl-4-hydroxypyridazin-3(2H)-one,
6-Cyclohexyl-4-hydroxypyridazin-3(2H)-one,
4-Hydroxy-6-isopropylpyridazin-3(2H)-one,
6-(Azetidin-1-yl)-4-hydroxypyridazin-3(2H)-one,
6-(Dimethylamino)-4-hydroxypyridazin-3(2H)-one,
4-Hydroxy-6-(methyl(propyl)amino)pyridazin-3(2H)-one,
6-(Ethyl(methyl)amino)-4-hydroxypyridazin-3(2H)-one,
4-Hydroxy-6-(piperidin-1-yl)pyridazin-3(2H)-one,
6-tert-Butyl-4-hydroxypyridazin-3(2H)-one,
and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises (i) when $R^2$ represents an optionally substituted $C_2$-$C_8$ alkyl, $C_3$-$C_8$ cycloalkyl or tetrahydropyranyl group, hydrogenating a compound of formula (II)

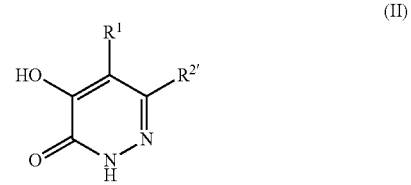

(II)

wherein $R^{2'}$ represents a moiety of formula (III)

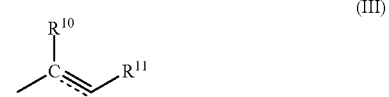

(III)

in which $R^{10}$ and $R^{11}$ each independently represent a hydrogen atom or an alkyl group wherein the total number of carbon atoms in $R^{10}$ and $R^{11}$ taken together is 0 or an integer in the range from 1 to 6, or $R^{10}$ and $R^{11}$ together with the carbon atoms to which they are attached form either a 3- to 8-membered cycloalkenyl ring, or, a ring of formula (IV)

(IV)

the moiety of formula (III) being optionally substituted with one or more substituents as defined for the optional substituents in $R^2$ in formula (I), and $R^1$ is as defined in formula (I); or (ii) when $R^2$ represents a group —$NR^3R^4$, reacting a compound of formula (V)

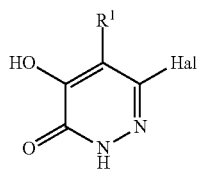

(V)

in which Hal represents a halogen atom such as chlorine and $R^1$ is as defined in formula (I), with a compound of formula (VI), $HNR^3R^4$, in which $R^3$ and $R^4$ are as defined in formula (I);

and optionally thereafter carrying out one or more of the following procedures:
 converting a compound of formula (I) into another compound of formula (I)
 removing any protecting groups
 forming a pharmaceutically acceptable salt.

Process (i) may conveniently be carried out according to techniques known in the art, e.g. in the presence of an organic solvent such as ethanol using hydrogen gas and a palladium on carbon catalyst, under acid catalysed conditions as required.

Process (ii), an amination reaction, may conveniently be carried out in an organic solvent such as toluene in the presence of (1) a palladium catalyst such as tris(dibenzylideneacetone)dipalladium(0) ($Pd_2(DBA)_3$), (2) a base such as sodium tert-butoxide and (3) an organophosphorous compound such as 4,5-bis(diphenylphosphino)-9,9-dimethylxanthene (Xantphos).

Compounds of formulae (II), (V) and (VI) are either commercially available, are well known in the literature or may be prepared using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-naphthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Compounds of formula (I) and their salts may be in the form of hydrates or solvates which form an aspect of the present invention. Such solvates may be formed with common organic solvents, including but not limited to alcoholic solvents, e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as D-amino acid oxidase enzyme (DAAO) inhibitors, and thus may be used in the treatment of schizophrenia and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder and disruptive behaviour disorders), pain (e.g. neuropathic pain) and/or neurodegenerative disorders (e.g. Parkinson's or Alzheimer's disease).

Thus, the present invention provides a compound of formula (I) or a pharmaceutically acceptable salt thereof as hereinbefore defined, for use in therapy, in particular for the treatment of conditions whose development or symptoms are linked to DAAO enzyme activity.

The present invention also provides the use of a compound of formula (I) or a pharmaceutically acceptable salt thereof as hereinbefore defined, for the preparation of a medicament for the treatment of conditions whose development or symptoms are linked to DAAO enzyme activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition, or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning) or pain (such as neuropathic pain).

The invention also provides a method of treating at least one symptom or condition associated with schizophrenia, schizophreniform disorder, schizoaffective disorder and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder, autistic spectrum disorders and disruptive behaviour disorders), pain (e.g. neuropathic pain) and/or neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorders.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant such as that described in Ph. Helv. or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions and/or with serine (D-SER). Combination compositions which result from such an approach also form an aspect of the present invention.

The invention therefore further relates to combination therapies wherein a compound of the invention or a pharmaceutical composition or formulation comprising a compound of the invention is administered with another therapeutic agent or agents and/or with serine, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluopcrazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrigine, and gabapentin, and equivalents and pharmaceutically active isomer(s) and/or metabolite(s) thereof;

(vi) Alzheimer's therapies including, for example, donepezil, memantine, tacrine, and equivalents and pharmaceutically active isomer(s) and/or metabolite(s) thereof;

(vii) Parkinson's therapies including, for example, deprenyl, L-dopa, Requip, Mirapex, monoamine oxidase type B (MAO-B) inhibitors such as selegiline and rasagiline, catechol-O-methyl transferase (COMT) inhibitors such as Tasmar, A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;

(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;

(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;

(xi) neuropathic pain therapies including, for example, gabapentin, lidoderm, and pregablin, and equivalents and pharmaceutically active isomer(s) and/or metabolite(s) thereof;

(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;

(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xv) 5HT1B ligands such as, for example, compounds disclosed in WO 99/05134 and WO 02/08212;

(xvi) mGluR2 agonists;

(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xviii) chemokine receptor CCRI inhibitors; and (xix) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Any novel intermediates described below are also to be considered an aspect of the present invention.

Nuclear magnetic resonance (NMR) spectra were recorded at 400 MHz; the chemical shifts (δ) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia.

Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative High Performance Liquid Chromatography (HPLC) was performed using an Agilent Technologies 1100 Series system typically using Waters 19 mm id×100 mm long C18 columns such as XBridge or SunFire 5 μm materials at 20 mL/min. Mobile phases typically consisted of acetonitrile or methanol mixed with water containing either 0.1% formic acid or 0.1% ammonia, unless stated otherwise.

In the following descriptions "room temperature" denotes a temperature in the range from 20° C. to 25° C.

The abbreviations used in the specific examples have the following meanings:
DMSO Dimethyl sulfoxide
DMSO-d$_6$ Deuterated dimethyl sulfoxide
DMF N,N-Dimethylformamide
MS Mass spectrum
NMR Nuclear magnetic resonance
MgSO$_4$ Magnesium sulphate
DBU 2,3,4,6,7,8,9,10-Octahydropyrimido[1,2-a]azepine
CD$_2$Cl$_2$ Deuterated dichloromethane

1. INTERMEDIATES

Scheme 1:

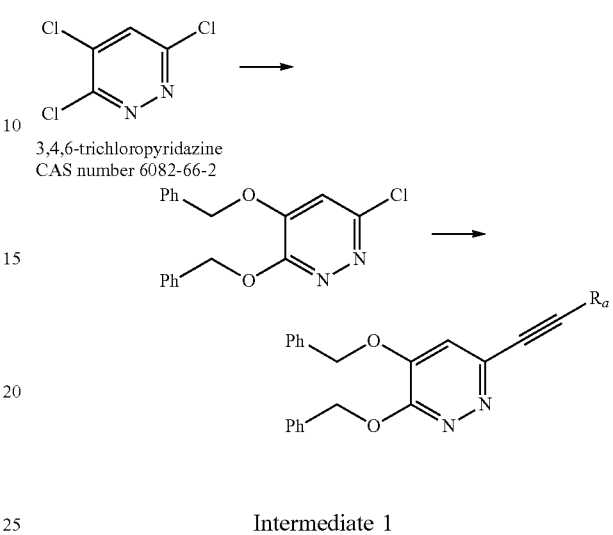

Intermediate 1

3,4-bis(Benzyloxy)-6-(3-methylbut-1-ynyl)pyridazine (i) 3,4-bis(Benzyloxy)-6-chloropyridazine Phenylmethanol (6.72 g, 62.2 mmol) was added dropwise to a suspension of sodium hydride (60% suspension in mineral oil; 2.486 g, 62.2 mmol) in tetrahydrofuran (100 ml) at room temperature. The resulting mixture was stirred for 1 hour and then cooled to 0° C. before 3,4,6-trichloropyridazine (5.7 g, 31.1 mmol) was added portion-wise over 10 minutes. The reaction was then allowed to warm to room temperature and stirred for 16 hours before being poured into water and extracted with ethyl acetate (twice). The organic layer was washed with brine, dried (MgSO$_4$) and evaporated. The residue was purified by silica chromatography (eluting with 5-20% ethyl acetate in petrol containing 5% tetrahydrofuran) to yield 3,4-bis(benzyloxy)-6-chloropyridazine (4.0 g, 12.24 mmol, 39% yield) as the major product.

$^1$H NMR (400 MHz, DMSO-d$_6$): δ ppm 7.31-7.52 (m, 11 H) 5.51 (s, 2 H) and 5.31 (s, 2 H).

(ii) 3,4-bis(Benzyloxy)-6-(3-methylbut-1-ynyl)pyridazine

A round-bottomed flask was charged with copper(I) iodide (0.044 g, 0.230 mmol), bis(triphenylphosphine)palladium(II) chloride (0.322 g, 0.459 mmol) and 3,4-bis(benzyloxy)-6-chloropyridazine (2.5 g, 7.65 mmol) and the reaction vessel evacuated and purged with nitrogen. DMF (25.5 ml) and then DBU (6.92 ml, 45.9 mmol) were added under vacuum and the reaction was flushed with nitrogen and heated to 80° C. for 1 hour.

Upon cooling the resulting mixture was washed with water and extracted into ethyl acetate. The combined organics were then washed with brine (half saturated, ×5), dried (MgSO$_4$) and concentrated in vacuo. The residue was purified by silica chromatography eluting with 0-50% ethyl acetate/petrol and the appropriate fractions combined and concentrated to give a yellow oil (2.43 g, 89%).

$^1$H NMR (400 MHz, DMSO-d$_6$) δ 7.25-7.58 (m, 11 H), 5.53 (s, 2 H), 5.27 (s, 2 H), 2.81-2.94 (m, 1 H) and 1.21-1.29 (m, 6 H).

MS ES$^+$: 359.

Scheme 2:

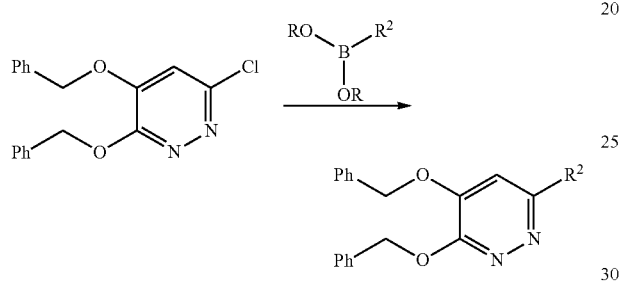

Intermediate 2

3,4-bis(Benzyloxy)-6-cyclopropylpyridazine

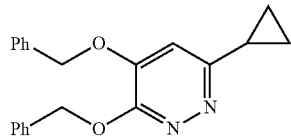 [SMILES: c1ccc(COc2cc(C3CC3)nnc2OCc2ccccc2)cc1]

To a mixture of 3,4-bis(benzyloxy)-6-chloropyridazine (prepared as described in step (i) of Intermediate 1; 500 mg, 1.53 mmol) in water (2 ml) and tetrahydrofuran (4 ml) was added cyclopropylboronic acid (263 mg, 3.06 mmol), tetrakis(triphenyl-phosphine)palladium(0) (177 mg, 0.153 mmol) and potassium phosphate (tribasic; 1 g, 4.7 mmol). The reaction vessel was evacuated and purged with nitrogen and then heated under microwave irradiation at 100° C. for 1 hour. It was then partitioned between ethyl acetate and water and the organic extracts were washed with further water and brine and concentrated under reduced pressure to give a pale brown solid which was purified using silica chromatography eluting with (0-100% ethyl acetate in petrol).

$^1$H NMR (400 MHz, CD$_2$Cl$_2$) δ 7.43-7.73 (m, 10 H), 6.78 (s, 1 H), 5.71 (s, 2 H), 5.33 (s, 2 H), 2.02-2.32 (m, 1 H) and 0.65-0.88 (m, 4 H).

MS ES$^+$: 333.

Intermediate 3

3,4-bis(Benzyloxy)-6-(3,6-dihydro-2H-pyran-4-yl)pyridazine

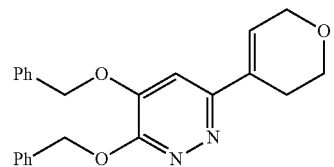 [SMILES: C1=C(c2cc(OCc3ccccc3)c(OCc3ccccc3)nn2)CCOC1]

Prepared as described for 3,4-bis(benzyloxy)-6-cyclopropylpyridazine (Intermediate 2) from 3,4-bis(benzyloxy)-6-chloropyridazine (Intermediate 1, step (i)) and 2-(3,6-dihydro-2H-pyran-4-yl)-4,4,5,5-tetramethyl-1,3,2-dioxaborolane in 66% yield.

$^1$H NMR (400 MHz, CD$_2$Cl$_2$) δ 7.25-7.58 (m, 10 H), 6.97 (s, 1 H), 6.32-6.48 (m, 1 H), 5.54-5.64 (m, 2 H), 5.11-5.23 (m, 2 H), 4.26-4.37 (m, 2 H), 3.85-3.95 (m, 2 H) and 2.61-2.76 (m, 2 H).

MS ES$^+$: 375.

Intermediate 4

3,4-bis(Benzyloxy)-6-(2-methylprop-1-en-1-yl)pyridazine

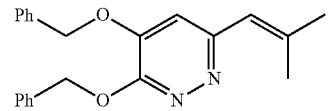 [SMILES: CC(C)=Cc1cc(OCc2ccccc2)c(OCc2ccccc2)nn1]

Prepared as described for 3,4-bis(benzyloxy)-6-cyclopropylpyridazine (Intermediate 2) from 3,4-bis(benzyloxy)-6-chloropyridazine (Intermediate 1, step (i)) and 4,4,5,5-tetramethyl-2-(2-methylprop-1-enyl)-1,3,2-dioxaborolane using potassium carbonate as base in 58% yield.

$^1$H NMR (400 MHz, CD$_2$Cl$_2$) δ 7.28-7.57 (m, 10 H), 6.67 (s, 1 H), 6.23 (s, 1 H), 5.59 (s, 2 H), 5.14-5.19 (m, 2 H) and 1.90-2.05 (m, 6 H).

MS ES$^+$: 347.

Intermediate 5

3,4-bis(Benzyloxy)-6-(cyclopent-1-en-1-yl)pyridazine

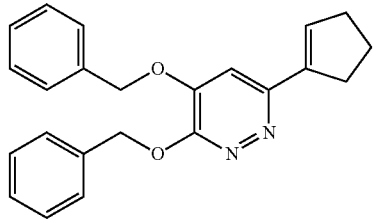 [SMILES: C1=C(c2cc(OCc3ccccc3)c(OCc3ccccc3)nn2)CCC1]

A microwave vial was charged with a mixture of 3,4-bis(benzyloxy)-6-chloropyridazine (Intermediate 1, step (i); 1.0 g, 3.06 mmol), dioxane (6.8 ml) and water (3.4 ml) and then degassed and to this was added mono(bis(di-tert-butyl(4-(dimethylamino)phenyl)-phosphonio)palladium(IV))dichloride (65 mg, 0.092 mmol), potassium carbonate (1.48 g, 10.71 mmol) and cyclopentenylboronic acid (685 mg, 6.12 mmol). The mixture was heated to 120° C. for 1 hour and upon cooling was partitioned between ethyl acetate and water and the organic layer was washed with brine, dried (MgSO$_4$), filtered and concentrated. The crude material was purified by silica chromatography eluting with 0-50% ethyl acetate in petrol to afford the title compound as a pale yellow solid (99% yield).

$^1$H NMR (400 MHz, DMSO-d$_6$) δ 7.26-7.56 (m, 11 H), 6.64 (br s, 1 H), 5.52 (s, 2 H), 5.29 (s, 2 H), 2.71-2.84 (m, 2 H), 2.26-2.36 (m, 2 H) and 1.90-2.03 (m, 2 H).

MS ES$^+$: 359.

Intermediate 6

3,4-bis(Benzyloxy)-6-(cyclohex-1-en-1-yl)pyridazine

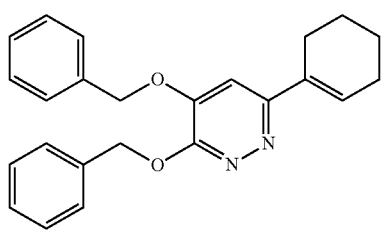 [SMILES: C1=C(c2cc(OCc3ccccc3)c(OCc3ccccc3)nn2)CCCC1]

Prepared as described for Intermediate 5 from 3,4-bis(benzyloxy)-6-chloropyridazine (Intermediate 1, step (i)) and cyclohexenylboronic acid in 39% yield.

$^1$H NMR (400 MHz, CD$_2$Cl$_2$) δ 7.28-7.55 (m, 10 H), 6.97 (s, 1 H), 6.36-6.47 (m, 1 H), 5.51-5.65 (m, 2 H), 5.06-5.23 (m, 2 H), 2.52-2.66 (m, 2 H), 2.17-2.32 (m, 2 H) and 1.59-1.90 (m, 4 H).

MS ES$^+$: 373.

Intermediate 7

3,4-bis(Benzyloxy)-6-(prop-1-en-2-yl)pyridazine

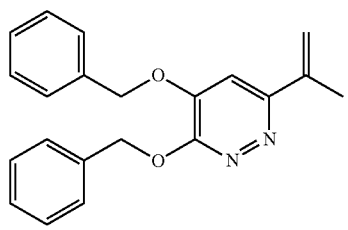 [SMILES: C=C(C)c1cc(OCc2ccccc2)c(OCc2ccccc2)nn1]

Prepared as described for Intermediate 5 from 3,4-bis(benzyloxy)-6-chloropyridazine (Intermediate 1, step (i)) and 4,4,5,5-tetramethyl-2-(prop-1-en-2-yl)-1,3,2-dioxaborolane in 73% yield.

$^1$H NMR (400 MHz, CD$_2$Cl$_2$) δ ppm 7.51-7.61 (m, 2 H), 7.34-7.51 (m, 8 H), 7.12 (s, 1 H), 5.71 (br. s., 1 H), 5.64 (s, 2 H), 5.45 (br s, 1 H), 5.26 (s, 2 H) and 2.30 (s, 3 H).

Scheme 3:

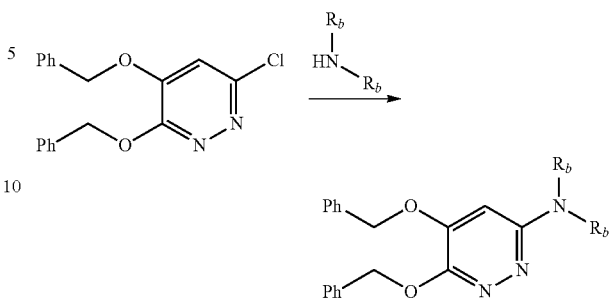

Intermediate 8

6-(Azetidin-1-yl)-3,4-bis(benzyloxy)pyridazine

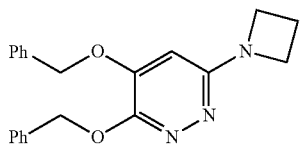 [SMILES: c1ccc(COc2cc(N3CCC3)nnc2OCc2ccccc2)cc1]

A microwave vial was charged 3,4-bis(benzyloxy)-6-chloropyridazine (Intermediate 1, step (i); 1 g, 3.06 mmol), sodium tert-butoxide (0.588 g, 6.12 mmol) and [1,3-bis(2,4,6-trimethylphenyl)-2,3-dihydro-1H-imidazol-2-yl](chloro)palladium-prop-1-ene (1:1) (0.150 g, 0.306 mmol) in dry dimethoxyethane (10.20 ml). The reaction was degassed and purged with nitrogen. To this was then added azetidine (0.349 g, 6.12 mmol) before the whole was heated under microwave irradiation at 80° C. for 1.5 hours. The resulting mixture was diluted with ethyl acetate and water and the organics were washed with water and brine, dried (MgSO$_4$), filtered and concentrated to give a yellow oil. The crude product was purified by silica chromatography eluting with 0-100% ethyl acetate petrol to afford the crude product (ca. 50% yield) which was deprotected without further purification.

MS ES$^+$: 348.

Intermediate 9

5,6-bis(Benzyloxy)-N,N-dimethylpyridazin-3-amine

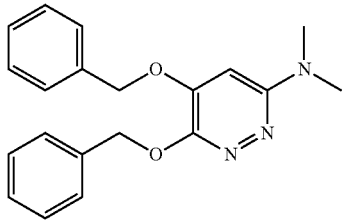 [SMILES: CN(C)c1cc(OCc2ccccc2)c(OCc2ccccc2)nn1]

Prepared as described for 6-(azetidin-1-yl)-3,4-bis(benzyloxy)pyridazine (Intermediate 8) from 3,4-bis(benzyloxy)-6-chloropyridazine (Intermediate 1, step (i)) and dimethylamine in 76% yield.

¹H NMR (400 MHz, CD₂Cl₂) δ ppm 7.17-7.57 (m, 10 H), 6.28 (s, 1 H), 5.46 (s, 2 H), 5.14 (s, 2 H) and 3.03 (s, 6 H).
MS ES⁺: 336.

Intermediate 10

5,6-bis(Benzyloxy)-N-methyl-N-propylpyridazin-3-amine

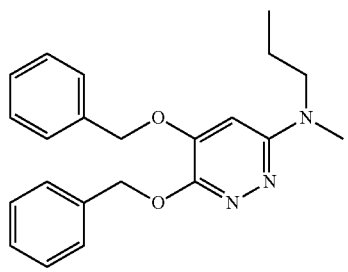 [SMILES: CCCN(C)c1cc(OCc2ccccc2)c(OCc2ccccc2)nn1]

Prepared as described for 6-(azetidin-1-yl)-3,4-bis(benzyloxy)pyridazine (Intermediate 8) from 3,4-bis(benzyloxy)-6-chloropyridazine (Intermediate 1, step (i)) and N-methylpropan-1-amine in 13% yield.

¹H NMR (400 MHz, CD₂Cl₂) δ 7.25-7.52 (m, 10 H), 6.21 (s, 1 H), 5.45 (s, 2 H), 5.10-5.20 (m, 2 H), 3.30-3.41 (m, 2 H), 3.02 (s, 3 H), 1.45-1.60 (m, 2 H) and 0.82-0.93 (m, 3 H).
MS ES⁺: 364.

Intermediate 11

5,6-bis(Benzyloxy)-N-ethyl-N-methylpyridazin-3-amine

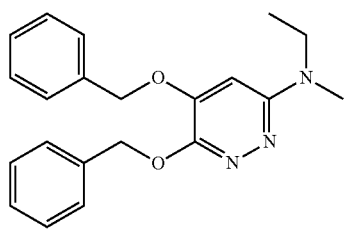 [SMILES: CCN(C)c1cc(OCc2ccccc2)c(OCc2ccccc2)nn1]

Prepared as described for 6-(azetidin-1-yl)-3,4-bis(benzyloxy)pyridazine (Intermediate 8) from 3,4-bis(benzyloxy)-6-chloropyridazine (Intermediate 1, step (i)) and N-methylethanamine in 9% yield.

¹H NMR (400 MHz, CD₃OD) δ 7.27-7.53 (m, 10 H), 6.20-6.27 (m, 1 H), 5.45 (s, 2 H), 5.14 (s, 2 H), 3.44-3.54 (m, 2 H), 2.99 (s, 3 H) and 1.04-1.12 (m, 3 H).
MS ES⁺: 350.

Intermediate 12

3,4-bis(Benzyloxy)-6-(piperidin-1-yl)pyridazine

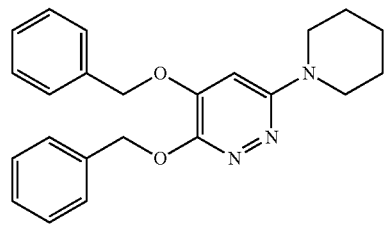 [SMILES: c1ccc(COc2cc(N3CCCCC3)nnc2OCc2ccccc2)cc1]

Prepared as described for 6-(azetidin-1-yl)-3,4-bis(benzyloxy)pyridazine (Intermediate 8) from 3,4-bis(benzyloxy)-6-chloropyridazine (Intermediate 1, step (i)) and piperidine in 39% yield.

¹H NMR (400 MHz, CD₂Cl₂) δ 7.27-7.53 (m, 10 H), 6.41 (s, 1 H), 5.46 (s, 2 H), 5.12 (s, 2 H), 3.43 (br s, 4 H) and 1.57-1.73 (m, 6 H).
MS ES⁺: 376.

Scheme 4:

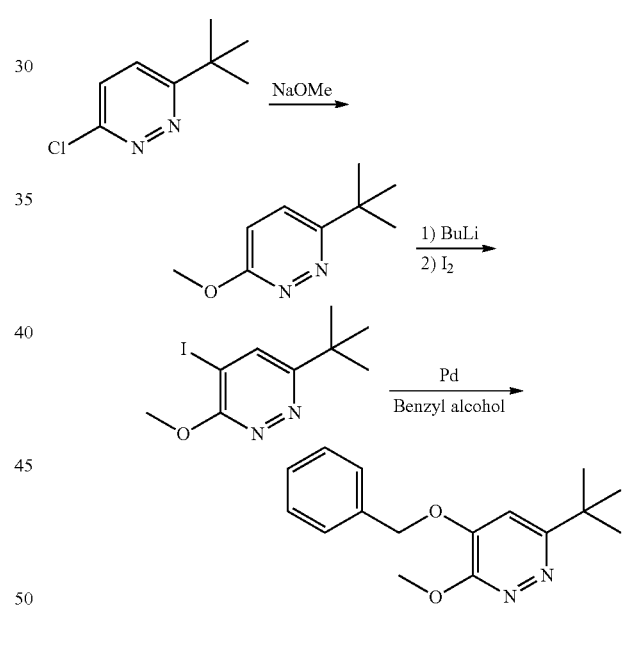

Intermediate 13

3-tert-Butyl-6-methoxypyridazine

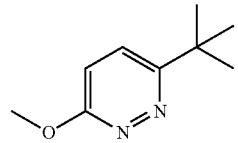

To a solution of 3-tert-butyl-6-chloropyridazine (2.0 g, 11.72 mmol) in methanol (30 ml) was added sodium methoxide solution (25 wt % in methanol; 5.36 ml, 23.44 mmol). The reaction mixture was stirred at room temperature for 2 hours and then heated to 50° C. for 2 hours. A further amount of sodium methoxide solution (25 wt % in methanol; 5.36 ml, 23.44 mmol) was added and the reaction mixture heated to 50° C. for 2 hours. A further amount of sodium methoxide solution (25 wt % in methanol; 5.36 ml, 23.44 mmol) was added and the reaction mixture heated to 50° C. for 60 hours before it was allowed to cool and quenched with water and partially concentrated to remove excess methanol. The residue was partitioned between water and ethyl acetate and the organic phase dried (MgSO$_4$) and concentrated in vacuo to give the title compound as a yellow oil, which crystallised on standing (1.79 g, 92%).

$^1$H NMR (400 MHz, CD$_2$Cl$_2$) δ 7.39-7.47 (m, 1 H), 6.84-6.93 (m, 1 H), 4.03-4.14 (m, 3 H) and 1.38 (s, 9 H).

MS ES$^+$ 167.

Intermediate 14

6-tert-Butyl-4-iodo-3-methoxypyridazine

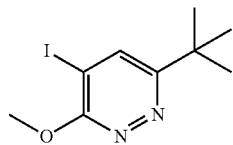

To a solution of 2,2,6,6-tetramethylpiperidine (1.051 ml, 6.38 mmol) in tetrahydrofuran (8 ml) at 0° C. was added n-butyl lithium (1.6 M in hexanes; 3.62 ml, 5.80 mmol). The resulting mixture was allowed to stir at 0° C. for 45 minutes and cooled to −20° C., followed by the addition of 3-tert-butyl-6-methoxypyridazine (Intermediate 13) (0.8 g, 4.81 mmol) in tetrahydrofuran (24 ml). The black solution was stirred at −20° C. for 30 minutes and added to a cold solution of iodine (1.47 g, 5.80 mmol) in tetrahydrofuran (32 ml) at −20° C. The reaction mixture was then stirred at −20° C. for 30 minutes before being quenched with methanol and saturated aqueous sodium bicarbonate solution and then extracted with ethyl acetate. The organic phase was washed with saturated aqueous sodium bicarbonate solution and brine, dried (MgSO$_4$) and concentrated in vacuo to a dark brown gum. The crude product was purified by silica chromatography, eluting with 0-10% ethyl acetate in petrol to give the title compound as a yellow solid (178 mg, 13%).

$^1$H NMR (400 MHz, CD$_2$Cl$_2$) δ 8.01 (s, 1 H), 4.17 (s, 3 H) and 1.43 (s, 9 H)

MS ES$^+$ 293.

Intermediate 15

4-(Benzyloxy)-6-tert-butyl-3-methoxypyridazine

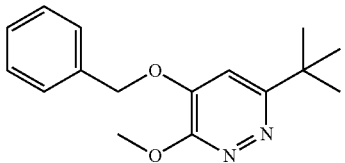 [SMILES: COc1nnc(C(C)(C)C)cc1OCc1ccccc1]

To a two-necked flask was added caesium carbonate (0.40 g, 1.22 mmol), palladium(II) acetate (14 mgs, 0.061 mmol), 1,1'-binaphthyl-2-yl di-tert-butylphosphine (49 mgs, 0.122 mmol) and toluene (3 ml). The mixture was degassed for 15 minutes followed by the addition of benzyl alcohol (0.064 ml, 0.612 mmol) and a solution of 6-tert-butyl-4-iodo-3-methoxypyridazine (Intermediate 14; 0.178 g, 0.61 mmol) in toluene (3 ml). The resulting mixture was heated to 90° C. for 60 hours before the reaction was quenched with water and extracted into ethyl acetate. The organic phase was washed with brine, dried (MgSO$_4$) and concentrated under reduced pressure. The crude product was purified by silica chromatography, eluting with 0-30% ethyl acetate in petrol to give the title compound as a yellow gum (68 mg, 41%).

$^1$H NMR (400 MHz, CD$_2$Cl$_2$) δ ppm 7.22-7.50 (m, 5 H), 6.87 (s, 1 H), 5.15 (s, 2 H), 4.08-4.15 (m, 3 H) and 1.38 (s, 9 H)

MS ES$^+$ 273.

Scheme 5:

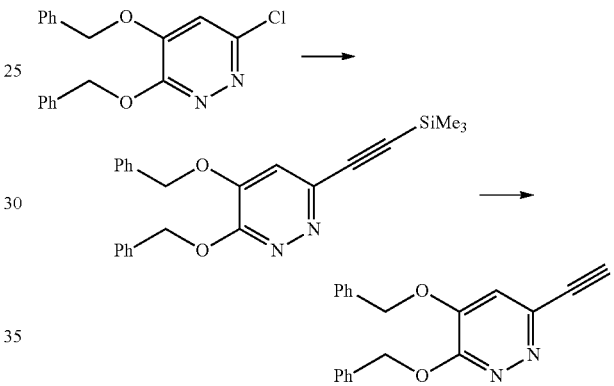

Intermediate 16

3,4-bis(Benzyloxy)-6-[(trimethylsilyl)ethynyl]pyridazine

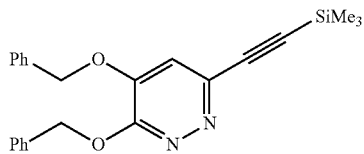 [SMILES: C[Si](C)(C)C#Cc1cc(OCc2ccccc2)c(OCc2ccccc2)nn1]

A 20 ml microwave vial was charged with 3,4-bis(benzyloxy)-6-chloropyridazine (Intermediate 1, step (i), 1 g, 3.06 mmol) and ethynyltrimethylsilane (902 mg, 9.18 mmol) in tetrahydrofuran (5 ml) to afford an orange solution. The reaction was purged with nitrogen before DBU (2.77 ml, 18.36 mmol), dichlorobis(triphenylphosphine)-palladium(II) (107 mg, 0.153 mmol) and copper(I) iodide (58.3 mg, 0.306 mmol) were added and the whole was subjected to microwave radiation for 1 hour at 80° C. Upon cooling, the reaction mixture was diluted with ethyl acetate and washed with brine. The organic layer was purified by silica chromatography (eluting with 0-30% ethyl acetate in petrol) to yield 3,4-bis(benzyloxy)-6-((trimethylsilyl)ethynyl)pyridazine (838 mg, 2.16 mmol, 70% yield)

¹H NMR (400 MHz, DMSO-d₆): δ 7.08-7.28 (m, 11 H), 5.32 (s, 2 H), 5.06 (s, 2 H) and 0.08 (s, 9 H)

MS ES⁺: 389.

Intermediate 17

3,4-bis(Benzyloxy)-6-ethynylpyridazine

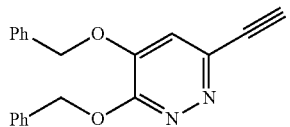 [SMILES: C#Cc1cc(OCc2ccccc2)c(OCc2ccccc2)nn1]

Potassium carbonate (295 mg, 2.136 mmol), 3,4-bis(benzyloxy)-6-((trimethylsilyl)ethynyl)pyridazine (Intermediate 16; 830 mg, 2.14 mmol) and methanol (10 ml) were added to tetrahydrofuran (5 ml) to produce an orange suspension. The mixture was stirred for 1 hour and then partitioned between brine and ethyl acetate. The organic layer was washed with brine and evaporated before the residue was purified by silica chromatography (eluting with 10-50% ethyl acetate in petrol) to yield 3,4-bis(benzyloxy)-6-ethynylpyridazine (530 mg, 1.68 mmol, 78% yield).

¹H NMR (400 MHz, DMSO-d₆): δ 7.31-7.53 (m, 11 H), 5.59 (s, 2 H), 5.30 (s, 2 H) and 4.53 (s, 1 H).

MS ES⁺: 317.

2. EXAMPLES

Example 1

6-Ethyl-4-hydroxypyridazin-3(2H)-one

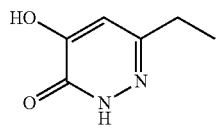

3,4-bis(Benzyloxy)-6-ethynylpyridazine (Intermediate 17; 650 mg 2.05 mmol) was dissolved in ethyl acetate (20 ml) and palladium on carbon (219 mgs, 0.205 mmol) was added before the mixture was purged and subjected to hydrogen gas. The reaction was then filtered and evaporated and the residue was purified by reverse phase HPLC to afford a cream solid (150 mg, 52% yield).

¹H NMR (400 MHz, DMSO-d₆) δ 12.63 (br s, 1 H), 10.52 (br s, 1 H), 6.53 (s, 1 H), 2.44 (s, 2 H) and 1.01-1.18 (m, 3 H).

MS ES⁺: 141.

Example 2

4-Hydroxy-6-(3-methylbutyl)pyridazin-3(2H)-one

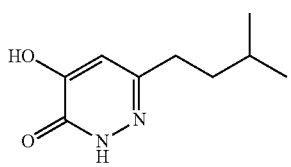

Prepared in the same way as 6-ethyl-4-hydroxypyridazin-3(2H)-one (Example 1) from 3,4-bis(benzyloxy)-6-(3-methylbut-1-ynyl)pyridazine (Intermediate 1) except that the solvent used for the hydrogenation was ethanol and the final compound was recrystallised from a mixture of ethyl acetate and heptane.

¹H NMR (400 MHz, DMSO-d₆) δ 12.63 (br s, 1 H), 10.66 (br s, 1 H), 6.53 (s, 1 H), 2.39-2.47 (m, 2 H), 1.38-1.57 (m, 3 H) and 0.88 (d, 6 H).

MS ES⁺: 183.

Example 3

6-Cyclopropyl-4-hydroxypyridazin-3(2H)-one

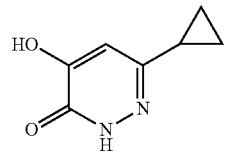 [SMILES: O=c1[nH]nc(C2CC2)cc1O]

Prepared in the same way as 6-ethyl-4-hydroxypyridazin-3(2H)-one (Example 1) from 3,4-bis(benzyloxy)-6-cyclopropylpyridazine (Intermediate 2) except that the solvent used for the hydrogenation was methanol and the crude product was purified by acidic reverse phase preparative HPLC before being recrystallised from ethyl acetate to afford a white solid (35% yield).

¹H NMR (400 MHz, DMSO-d₆) δ 12.60 (br s, 1 H), 10.51-10.84 (m, 1 H), 6.44 (s, 1 H), 1.70-1.92 (m, 1 H), 0.78-0.93 (m, 2 H) and 0.60-0.76 (m, 2 H).

MS ES⁺: 153.

Example 4

4-Hydroxy-6-(tetrahydro-2H-pyran-4-yl)pyridazin-3(2H)-one

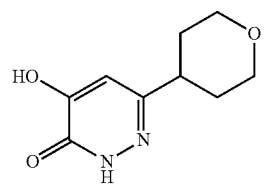

Prepared in the same way as 6-ethyl-4-hydroxypyridazin-3(2H)-one (Example 1) from 3,4-bis(benzyloxy)-6-(3,6-dihydro-2H-pyran-4-yl)pyridazine (Intermediate 3) except that the solvent mixture used for the hydrogenation was made up from water and tetrahydrofuran (1:2) and the final compound was recrystallised from a mixture of ethyl acetate and ethanol.

¹H NMR (400 MHz, DMSO-d₆) δ 6.34 (s, 1 H), 3.82-3.96 (m, 2 H), 3.32-3.41 (m, 2 H), 2.55-2.71 (m, 1 H) and 1.48-1.75 (m, 4 H).

MS ES⁺: 197.

Example 5

4-Hydroxy-6-(2-methylpropyl)pyridazin-3(2H)-one

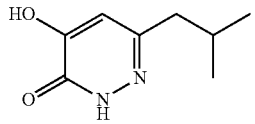

Prepared in the same way as 6-ethyl-4-hydroxypyridazin-3(2H)-one (Example 1) from 3,4-bis(benzyloxy)-6-(2-methylprop-1-en-1-yl)pyridazine (Intermediate 4) except that the product was recrystallised from ethyl acetate.

$^1$H NMR (400 MHz, DMSO-d$_6$) δ 12.66 (br s, 1 H), 10.65 (br s, 1 H), 6.52 (s, 1 H), 2.20-2.39 (m, 2 H), 1.81-2.03 (m, 1 H) and 0.79-0.95 (m, 6 H).

MS ES$^+$: 169.

Example 6

6-Cyclopentyl-4-hydroxypyridazin-3(2H)-one

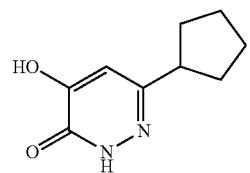 [SMILES: O=c1[nH]nc(C2CCCC2)cc1O]

Prepared in the same way as 6-ethyl-4-hydroxypyridazin-3(2H)-one (Example 1) from 3,4-bis(benzyloxy)-6-(cyclopent-1-en-1-yl)pyridazine (Intermediate 5) except that the solvent mixture used for the hydrogenation was made up from ethanol and tetrahydrofuran and the product was recrystallised from a mixture of heptane and ethyl acetate.

$^1$H NMR (400 MHz, DMSO-d$_6$) δ 12.61 (br s, 1 H), 10.65 (br s, 1 H), 6.54 (s, 1 H), 2.82-2.96 (m, 1 H), 1.80-1.97 (m, 2 H) and 1.49-1.76 (m, 6 H).

MS ES$^+$: 181.

Example 7

6-Cyclohexyl-4-hydroxypyridazin-3(2H)-one

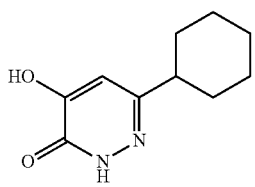 [SMILES: O=c1[nH]nc(C2CCCCC2)cc1O]

Prepared in the same way as 6-ethyl-4-hydroxypyridazin-3(2H)-one (Example 1) from 3,4-bis(benzyloxy)-6-(cyclohex-1-en-1-yl)pyridazine (Intermediate 6) except that the solvent used for the hydrogenation was ethanol and the product was recrystallised from ethyl acetate.

$^1$H NMR (400 MHz, DMSO-d$_6$) δ 12.65 (br s, 1 H), 10.64 (br s, 1 H), 6.57 (s, 1 H), 2.29-2.47 (m, 1 H), 1.51-1.91 (m, 5 H) and 1.04-1.45 (m, 5 H).

MS ES$^+$: 195.

Example 8

4-Hydroxy-6-isopropylpyridazin-3(2H)-one

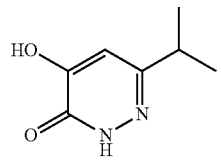

Prepared in the same way as 6-ethyl-4-hydroxypyridazin-3(2H)-one (Example 1) from 3,4-bis(benzyloxy)-6-(prop-1-en-2-yl)pyridazine (Intermediate 7) except that the solvent used for the hydrogenation was ethanol and the product was recrystallised from a mixture of ethyl acetate and methyl tert-butyl ether.

$^1$H NMR (400 MHz, CD$_2$Cl$_2$) δ 6.67 (s, 1 H), 2.79-2.94 (m, 1 H) and 1.16-1.28 (m, 6 H).

MS ES$^+$: 155.

Example 9

6-(Azetidin-1-yl)-4-hydroxypyridazin-3(2H)-one

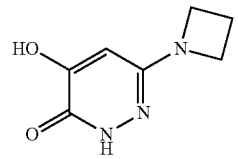 [SMILES: O=c1[nH]nc(N2CCC2)cc1O]

Prepared in the same way as 6-ethyl-4-hydroxypyridazin-3(2H)-one (Example 1) from 6-(azetidin-1-yl)-3,4-bis(benzyloxy)pyridazine (Intermediate 8) except that the product was purified by acidic normal phase preparatory HPLC (2% yield).

$^1$H NMR (400 MHz, CD$_3$OD) δ 6.12 (s, 1 H), 3.85-4.03 (m, 4 H) and 2.27-2.41 (m, 2 H).

MS ES$^+$: 168.

Example 10

6-(Dimethylamino)-4-hydroxypyridazin-3(2H)-one

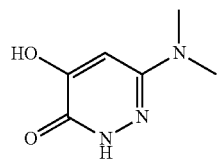

Prepared in the same way as 6-ethyl-4-hydroxypyridazin-3(2H)-one (Example 1) from 5,6-bis(benzyloxy)-N,N-dimethylpyridazin-3-amine (Intermediate 9) except that the product was purified by recrystallisation from ethanol to give the title compound as a pale brown solid (15% yield).

$^1$H NMR (400 MHz, DMSO-d$_6$) δ 12.0 (br s, 1 H), 10.5 (br s, 1 H), 6.55 (s, 1 H) and 2.84 (s, 6 H).
MS ES$^+$: 156.

Example 11

4-Hydroxy-6-(methyl(propyl)amino)pyridazin-3(2H)-one

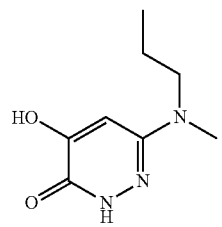

Prepared in the same way as 6-ethyl-4-hydroxypyridazin-3(2H)-one (Example 1) from 5,6-bis(benzyloxy)-N-methyl-N-propylpyridazin-3-amine (Intermediate 10) except that the crude material was recrystallised from a mixture of ethyl acetate and ethanol.
$^1$H NMR (400 MHz, DMSO-d$_6$) δ ppm 11.93 (br s, 1 H), 6.49 (s, 1 H), 3.12-3.23 (m, 2 H), 2.80 (s, 3 H), 1.40-1.53 (m, 2 H) and 0.84 (t, 3 H)
MS ES$^+$ 184.

Example 12

6-(Ethyl(methyl)amino)-4-hydroxypyridazin-3(2H)-one

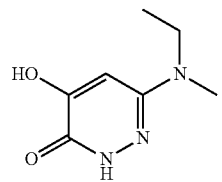

Prepared in the same way as 6-ethyl-4-hydroxypyridazin-3(2H)-one (Example 1) from 5,6-bis(benzyloxy)-N-ethyl-N-methylpyridazin-3-amine (Intermediate 11) but using tetrahydrofuran as solvent. The crude product was recrystallised from 2-propanol to give the title compound as a pale grey powder (22% yield).
$^1$H NMR (400 MHz, CD$_2$Cl$_2$) δ ppm 6.61 (s, 1 H), 3.39 (m, 2 H), 2.94 (s, 3 H) and 1.06-1.19 (m, 3 H).
MS ES$^+$ 170.

Example 13

4-Hydroxy-6-(piperidin-1-yl)pyridazin-3(2H)-one

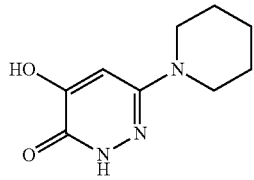 [SMILES: O=c1[nH]nc(N2CCCCC2)cc1O]

Prepared in the same way as 6-ethyl-4-hydroxypyridazin-3(2H)-one (Example 1) from 3,4-bis(benzyloxy)-6-(piperidin-1-yl)pyridazine (Intermediate 12) but purified by reverse phase C18 chromatography eluting with 5-100% aqueous methanol with a 0.1% formic acid modifier in both the water and methanol to give the title compound as a pale brown solid (31% yield).
$^1$H NMR (400 MHz, DMSO-d$_6$) δ ppm 12.03 (br s, 1 H), 10.43 (br s, 1 H), 6.59 (s, 1 H), 3.05-3.21 (m, 4 H) and 1.53 (br s, 6 H).
MS ES$^+$ 196.

Example 14

6-tert-Butyl-4-hydroxypyridazin-3(2H)-one

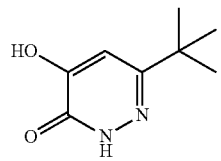

Acetic acid (0.086 ml, 1.498 mmol) and hydrobromic acid (0.149 ml, 2.75 mmol) were added to 4-(benzyloxy)-6-tert-butyl-3-methoxypyridazine (Intermediate 15; 0.068 g, 0.25 mmol) and the mixture was heated to 120° C. for 1 hour. A further portion of both acetic acid (0.086 ml, 1.498 mmol) and hydrobromic acid (0.149 ml, 2.75 mmol) were added and the reaction mixture heated to 150° C. overnight. Upon cooling it was loaded onto a C18 cartridge and the crude product purified by reverse phase chromatography, eluting with 0-100% aqueous acetonitrile with a 0.1% formic acid additive to each to afford the title compound as a pale cream solid (8.6 mg, 21% yield).
$^1$H NMR (400 MHz, DMSO-d$_6$) δ ppm 12.64 (br s, 1 H), 6.76 (s, 1 H) and 1.20 (s, 9 H).
MS ES$^+$ 169.

3. BIOLOGICAL EFFICACY OF COMPOUNDS OF THE INVENTION

In Vitro DAAO Enzyme Assay

The functional activity of compounds inhibiting the DAAO enzyme was determined by utilizing the co-product of the catalysis of D-Serine, H$_2$O$_2$, which can be quantitatively measured using the 'Amplex' (trade mark) Red (Invitrogen) detection. 'Amplex' Red reagent is a colorless substrate that reacts with hydrogen peroxide (H$_2$O$_2$) with a 1:1 stoichiometry to produce highly fluorescent resorufin (excitation/emission maxima=570/585 nm). The changes in fluorescence were monitored by a fluorescence plate reader, Envision (Perkin Elmer) and increases in DAAO activity were readily detected upon addition of D-Serine and suppression of this response observed with the application of test compounds.

Human DAAO enzyme was supplied by the Takeda Pharmaceutical Company (Osaka) and each batch was tested and used at concentrations giving comparable levels of activity. The $K_m$ of D-Serine was measured for each enzyme batch to maintain consistency; this $K_m$ was used in subsequent assays.

On the day of the assay compounds were serially diluted in DMSO before being diluted 1:20 with assay buffer (20 mM Tris ph 7.4). A 5 μl portion of assay buffer was added to the wells of a 384 clear base black-walled plate (Corning), 5 μl of diluted compound was then added via automated plate-to-plate transfer using the Bravo liquid handler (Agilent technologies) followed by 5 μl of human DAAO enzyme, and then 5 μl D-Serine 50 mM was added to all but the negative control wells (final concentration of 10 mM). Finally 5 μl 'Amplex' red reagent (Invitrogen) was added to all wells as per manufacturer's protocol. The plate was incubated for 60 minutes in the dark at 25° C. and the fluorescence in each well was measured in the Envision plate reader.

The $IC_{50}$ values for compounds were determined from ten-point half log scale dose-response studies and represent the concentration of compound required to provide 50% inhibition of DAAO activity in the presence of 10 mM D-Serine. Concentration response curves were generated using the average of duplicate wells for each data point and analyzed using non-linear regression and four parameter curve fit.

Results

| Example No. | Mean $IC_{50}$ (nM) | Example No. | Mean $IC_{50}$ (nM) |
|---|---|---|---|
| 1 | 11 | 2 | 61 |
| 3 | 40 | 4 | 4100 |
| 5 | 140 | 6 | 670 |
| 7 | 1100 | 8 | 36 |
| 9 | 2500 | 10 | 46 |
| 11 | 180 | 12 | 150 |
| 13 | 3600 | 14 | 44 |

These results indicate that compounds of the invention have potent inhibitory activity against the DAAO enzyme. The compounds tested above exhibit $IC_{50}$ values significantly less than 5 μM, with the most potent compounds showing activity at the DAAO enzyme with $IC_{50}$ values <250 nM. Accordingly, the compounds of the invention are expected to have usefulness in the prevention or treatment of conditions, such as those discussed above, in which DAAO enzyme activity is implicated.

The invention claimed is:

1. A compound of formula (I), or a pharmaceutically acceptable salt thereof:

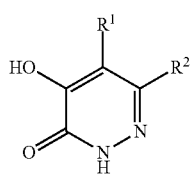

(I)

wherein
$R^1$ is chosen from a hydrogen or fluorine atom or a trifluoromethyl group;
$R^2$ is chosen from a $C_2$-$C_8$ alkyl, $C_3$-$C_8$ cycloalkyl, tetrahydropyranyl, or —$NR^3R^4$ group,
wherein the alkyl, cycloalkyl and tetrahydropyranyl groups are unsubstituted or substituted by at least one substituent chosen from halogen, hydroxyl, cyano, carboxyl, $C_1$-$C_6$ alkyl, difluoromethyl, trifluoromethyl, $C_1$-$C_6$ alkoxy, difluoromethoxy or trifluoromethoxy;
$R^3$ and $R^4$ are each independently chosen from a hydrogen atom or a $C_1$-$C_6$ alkyl group, or $R^3$ and $R^4$ together with the nitrogen atom to which they are attached form a saturated or unsaturated 4- to 8-membered heterocyclic ring, wherein each alkyl group or the heterocyclic ring is unsubstituted or substituted by at least one substituent chosen from halogen, hydroxyl, cyano, carboxyl, $C_1$-$C_6$ alkyl, difluoromethyl, trifluoromethyl, $C_1$-$C_6$ alkoxy, difluoromethoxy or trifluoromethoxy;
with the proviso that the compound of formula (I) is not:
2,3-dihydro-4-hydroxy-6-morpholinopyridazin-3-one, or
6-amino-4-hydroxy-pyridazinone.

2. The compound according to claim 1, wherein $R^1$ represents a hydrogen atom.

3. The compound according to claim 1, wherein $R^2$ is chosen from a $C_2$-$C_6$ alkyl or $C_3$-$C_6$ cycloalkyl group.

4. The compound according to claim 1, wherein $R^2$ represents a —$NR^3R^4$ group, and wherein $R^3$ and $R^4$ are each independently chosen from a hydrogen atom or a $C_1$-$C_4$ alkyl group.

5. The compound according to claim 1, wherein $R^2$ represents a —$NR^3R^4$ group, and wherein $R^3$ and $R^4$ together with the nitrogen atom to which they are attached form a saturated or unsaturated 4- to 6-membered heterocyclic ring.

6. The compound according to claim 5, wherein the heterocyclic ring is chosen from an azetidinyl, pyrrolyl, piperidinyl, morpholinyl, thiomorpholinyl, thiazolyl, piperazinyl, pyrazolyl, pyrazinyl, imidazolyl, isoxazolyl, triazolyl, tetrazolyl or pyridinyl moiety.

7. The compound according claim 1, wherein $R^2$ is chosen from a $C_2$-$C_8$ alkyl, $C_3$-$C_8$ cycloalkyl, tetrahydropyranyl, or —$NR^3R^4$ group,
wherein the alkyl, cycloalkyl and tetrahydropyranyl groups are unsubstituted or substituted by at least one substituent chosen from cyano, fluorine, chlorine, difluoromethyl, difluoromethoxy, trifluoromethyl, trifluoromethoxy, methyl or methoxy;
$R^3$ and $R^4$ are each independently chosen from a hydrogen atom or a $C_1$-$C_6$ alkyl group, or $R^3$ and $R^4$ together with the nitrogen atom to which they are attached form a saturated or unsaturated 4- to 8-membered heterocyclic ring,
wherein each alkyl group or the heterocyclic ring is unsubstituted or substituted by at least one substituent chosen from cyano, fluorine, chlorine, difluoromethyl, difluoromethoxy, trifluoromethyl, trifluoromethoxy, methyl or methoxy.

8. The compound according to claim 1, wherein
$R^1$ represents a hydrogen atom; and
$R^2$ is chosen from a $C_2$-$C_5$ alkyl, $C_3$-$C_6$ cycloalkyl, tetrahydropyranyl, or —$NR^3R^4$ group,
wherein $R^3$ and $R^4$ are each independently chosen from a $C_1$-$C_3$ alkyl group, or $R^3$ and $R^4$ together with the nitrogen atom to which they are attached form a saturated 4- to 6-membered heterocyclic ring.

9. The compound according to claim 1 chosen from:
6-Ethyl-4-hydroxypyridazin-3 (2H)-one,
4-Hydroxy-6-(3-methylbutyl)pyridazin-3 (2H)-one,
6-Cyclopropyl-4-hydroxypyridazin-3 (2H)-one,
4-Hydroxy-6-(tetrahydro-2H-pyran-4-yl)pyridazin-3 (2H)-one,
4-Hydroxy-6-(2-methylpropyl)pyridazin-3 (2H)-one,
6-Cyclopentyl-4-hydroxypyridazin-3(2H)-one,
6-Cyclohexyl-4-hydroxypyridazin-3 (2H)-one, 4-Hydroxy-6-isopropylpyridazin-3 (2H)-one,
6-(Azetidin-1-yl)-4-hydroxypyridazin-3 (2H)-one,
6-(Dimethylamino)-4-hydroxypyridazin-3 (2H)-one,
4-Hydroxy-6-(methyl(propyl)amino)pyridazin-3 (2H)-one,
6-(Ethyl(methyl)amino)-4-hydroxypyridazin-3 (2H)-one,
4-Hydroxy-6-(piperidin-1-yl)pyridazin-3(2H)-one,
6-tert-Butyl-4-hydroxypyridazin-3(2H)-one,
or a pharmaceutically acceptable salt thereof.

10. The compound according to claim 2, wherein $R^2$ is chosen from a $C_2$-$C_6$ alkyl or $C_3$-$C_6$ cycloalkyl group.

11. The compound according to claim 2, wherein $R^2$ represents a —$NR^3R^4$ group, and wherein $R^3$ and $R^4$ are each independently chosen from a hydrogen atom or a $C_1$-$C_4$ alkyl group.

12. The compound according to claim 2, wherein $R^2$ represents a —$NR^3R^4$ group, and wherein $R^3$ and $R^4$ together with the nitrogen atom to which they are attached form a saturated or unsaturated 4- to 6-membered heterocyclic ring.

13. The compound according to claim 12, wherein the heterocyclic ring is chosen from an azetidinyl, pyrrolyl, piperidinyl, morpholinyl, thiomorpholinyl, thiazolyl, piperazinyl, pyrazolyl, pyrazinyl, imidazolyl, isoxazolyl, triazolyl, tetrazolyl or pyridinyl moiety.

14. The compound according claim 2, wherein $R^2$ is chosen from a $C_2$-$C_8$ alkyl, $C_3$-$C_8$ cycloalkyl, tetrahydropyranyl, or —$NR^3R^4$ group,
 wherein the alkyl, cycloalkyl and tetrahydropyranyl groups are unsubstituted or substituted by at least one substituent chosen from cyano, fluorine, chlorine, difluoromethyl, difluoromethoxy, trifluoromethyl, trifluoromethoxy, methyl or methoxy;
 $R^3$ and $R^4$ are each independently chosen from a hydrogen atom or a $C_1$-$C_6$ alkyl group, or $R^3$ and $R^4$ together with the nitrogen atom to which they are attached form a saturated or unsaturated 4- to 8-membered heterocyclic ring,
 wherein each alkyl group or the heterocyclic ring is unsubstituted or substituted by at least one substituent chosen from cyano, fluorine, chlorine, difluoromethyl, difluoromethoxy, trifluoromethyl, trifluoromethoxy, methyl or methoxy.

15. A pharmaceutical composition comprising the compound according to claim 1 and a pharmaceutically acceptable adjuvant, diluent or carrier.

16. A combination of the compound according to claim 1 and at least one agent chosen from carbamazepine, olanzapine, quetiapine, verapamil, lamotrigine, oxcarbazepine, risperidone, aripiprazole, ziprasidone or lithium.

17. A process for the preparation of the compound according to claim 1, comprising:
 (i) when $R^2$ represents an unsubstituted or substituted $C_2$-$C_8$ alkyl, $C_3$-$C_8$ cycloalkyl or tetrahydropyranyl group, hydrogenating a compound of formula (II)

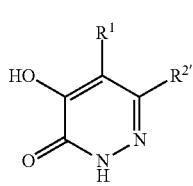

(II)

wherein $R^{2'}$ represents a moiety of formula (III)

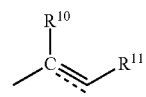

(III)

wherein $R^{10}$ and $R^{11}$ are each independently chosen from a hydrogen atom or an alkyl group, and wherein the total number of carbon atoms in $R^{10}$ and $R^{11}$ taken together is 0 or an integer in the range from 1 to 6, or $R^{10}$ and $R^{11}$ together with the carbon atoms to which they are attached form either a 3- to 8-membered cycloalkenyl ring, or, a ring of formula (IV)

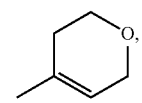

(IV)

wherein the moiety of formula (III) is unsubstituted or substituted with at least one substituent chosen from halogen, hydroxyl, cyano, carboxyl, $C_1$-$C_6$ alkyl, difluoromethyl, trifluoromethyl, $C_1$-$C_6$ alkoxy, difluoromethoxy or trifluoromethoxy; or
 (ii) when $R^2$ represents a group —$NR^3R^4$, reacting a compound of formula (V)

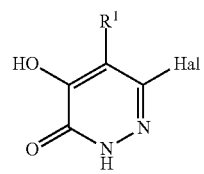

(V)

wherein Hal represents a halogen atom, with a compound of formula (VI), $HNR^3R^4$, wherein $R^3$ and $R^4$ are each independently chosen from a hydrogen atom or a $C_1$-$C_6$ alkyl group, or $R^3$ and $R^4$ together with the nitrogen atom to which they are attached form a saturated or unsaturated 4-to 8-membered heterocyclic ring, wherein each alkyl group or the heterocyclic ring is unsubstituted or substituted by at least one substituent chosen from halogen, hydroxyl, cyano, carboxyl, $C_1$-$C_6$ alkyl, difluoromethyl, trifluoromethyl, $C_1$-$C_6$ alkoxy, difluoromethoxy or trifluoromethoxy;
and optionally thereafter carrying out at least one of the following procedures:
 converting the compound according to claim 1 into another compound according to claim 1;
 removing any protecting groups; or
 forming a pharmaceutically acceptable salt.

18. A method of treating schizophrenia, schizophreniform disorder, schizoaffective disorder, cognitive disorders or pain comprising administering to a patient in need thereof a pharmaceutically effective amount of the compound according to claim 1.

\* \* \* \* \*